(12) United States Patent
Fitzgerald et al.

(10) Patent No.: US 6,417,777 B2
(45) Date of Patent: Jul. 9, 2002

(54) PRESSURE SENSITIVE MAT WITH BREATHING TUBE APPARATUS

(75) Inventors: Sanford G. Fitzgerald, Tulsa; Toby E. Smith, Broken Arrow, both of OK (US)

(73) Assignee: Bed-Check Corporation, Tulsa, OK (US)

( * ) Notice: Subject to any disclaimer, the term of this patent is extended or adjusted under 35 U.S.C. 154(b) by 0 days.

(21) Appl. No.: 09/792,001

(22) Filed: Feb. 23, 2001

Related U.S. Application Data

(60) Provisional application No. 60/184,424, filed on Feb. 23, 2000.

(51) Int. Cl.$^7$ .............................................. G08B 21/00
(52) U.S. Cl. ..................... 340/687; 340/573.1; 340/644
(58) Field of Search .............................. 340/573.1, 644, 340/650, 651, 652, 687, 573.5, 573.7, 575

(56) References Cited

U.S. PATENT DOCUMENTS

| | | | |
|---|---|---|---|
| 4,146,885 A | | 3/1979 | Lawson, Jr. |
| 4,158,628 A | | 6/1979 | Fleckensteim |
| 4,228,426 A | * | 10/1980 | Roberts .................... 340/573.4 |
| 4,484,043 A | | 11/1984 | Musick et al. |
| 4,565,910 A | | 1/1986 | Musick et al. |
| 4,700,180 A | * | 10/1987 | Vance ....................... 340/573.1 |
| 4,914,760 A | | 4/1990 | Hargest et al |
| 4,967,431 A | | 11/1990 | Hargest et al. |
| 5,029,352 A | | 7/1991 | Hargest et al. |
| 5,036,559 A | | 8/1991 | Hargest |
| 5,142,109 A | | 8/1992 | O'Meara, Jr. et al. |
| D361,462 S | | 8/1995 | Newham |
| 5,554,835 A | | 9/1996 | Newham |
| 5,600,108 A | | 2/1997 | Newham |
| 5,618,090 A | | 4/1997 | Montague et al. |
| 5,623,760 A | | 4/1997 | Newham |
| 5,633,627 A | | 5/1997 | Newham |
| 5,640,145 A | | 6/1997 | Newham |
| 5,654,694 A | | 8/1997 | Newham |
| 5,729,853 A | | 3/1998 | Thompson |
| 5,767,451 A | | 6/1998 | Röhling et al. |
| 5,864,108 A | | 1/1999 | Röhling et al. |
| 5,945,914 A | * | 8/1999 | Holmes et al. .............. 340/667 |
| 6,025,782 A | * | 2/2000 | Newham .................. 340/573.1 |
| 6,065,727 A | | 5/2000 | Fitzgerald et al. |
| 6,111,509 A | | 8/2000 | Holmes |
| 6,292,102 B1 | | 9/2001 | Smith et al. |
| 6,307,476 B1 | * | 10/2001 | Smith et al. .............. 340/573.1 |

FOREIGN PATENT DOCUMENTS

| | | |
|---|---|---|
| EP | 00221945 | 11/1992 |
| EP | 00226284 | 9/1993 |
| GB | 2 320 347 A | 6/1998 |
| WO | WO 90/10204 A1 | 9/1990 |
| WO | WO 09702882 | 1/1997 |
| WO | WO 09815763 | 4/1998 |
| WO | WO 98/18318 A1 | 5/1998 |

OTHER PUBLICATIONS

International Search Report prepared by the ISA/EP in connection with corresponding international application No. PCT/US01/06071 with a mailing date of Sep. 10, 2001.

* cited by examiner

Primary Examiner—Daniel J. Wu
(74) Attorney, Agent, or Firm—Fellers, Snider, Blankenship, Bailey & Tippens, P.C.

(57) ABSTRACT

This invention relates generally to patient monitoring systems and more particularly concerns devices and systems used to monitor bed patients in hospital or other care-giving environments. In accordance with a first aspect of the instant invention, there is provided a pressure sensitive mat which has been completely sealed around its exterior edges. The interior of the mat is kept in communication with the atmosphere by way of a section of flexible tubing which encloses the attached electrical line. One end of the tubing is sealed inside of the mat and the other end is open to the atmosphere, thereby providing a passageway for air to reach the interior of the mat. This arrangement, however, protects the interior of the mat from exposure to fluids near the perimeter of the mat and allows the mat-portion of the invention to be completely submersed without adverse effect, if that should become necessary.

20 Claims, 3 Drawing Sheets

PRESSURE SENSITIVE MAT WITH BREATHING TUBE APPARATUS

RELATED APPLICATIONS

This application claims priority from U.S. Provisional Patent Application No. 60/184,424 filed Feb. 23, 2000, the disclosure of which is incorporated herein by reference.

FIELD OF THE INVENTION

This invention relates generally to monitoring systems and, more particularly, concerns pressure-sensitive devices and systems used to monitor patients in hospital or other care giving environments.

BACKGROUND OF THE INVENTION

It is well documented that the elderly and post-surgical patients are at a heightened risk of falling. There are many reasons for this but, broadly speaking, these individuals are often afflicted by gait and balance disorders, weakness, dizziness, confusion, visual impairment, and postural hypotension (i.e., a sudden drop in blood pressure that causes dizziness and fainting), all of which are recognized as potential contributors to a fall. Additionally, cognitive and functional impairment, and sedating and psychoactive medications are also well recognized risk factors.

A fall places the patient at risk of various injuries including sprains, fractures, and broken bones—injuries which in some cases can be severe enough to eventually lead to a fatality. Of course, those most susceptible to falls are often those in the poorest general health and least likely to recover quickly from their injuries. In addition to the obvious physiological consequences of fall-related injuries, there are also a variety of adverse economic and legal consequences that include the actual cost of treating the victim and, in some cases, caretaker liability issues.

In the past, it has been commonplace to treat patients that are prone to falling by limiting their mobility through the use of restraints, the underlying theory being that if the patient is not free to move about, he or she will not be as likely to fall. However, research has shown that restraint-based patient treatment strategies are often more harmful than beneficial and should generally be avoided—the emphasis today being on the promotion of mobility rather than immobility. Among the more successful mobility-based strategies for fall prevention include interventions to improve patient strength and functional status, reduction of environmental hazards, and staff identification and monitoring of high-risk hospital patients and nursing home residents.

Of course, monitoring high-risk patients, as effective as that care strategy might appear to be in theory, suffers from the obvious practical disadvantage of requiring additional staff if the monitoring is to be in the form of direct observation. Thus, the trend in patient monitoring has been toward the use of electrical devices to signal changes in a patient's circumstance to a caregiver who might be located either nearby or remotely at a central monitoring facility, such as a nurse's station. The obvious advantage of an electronic monitoring arrangement is that it frees the caregiver to pursue other tasks away from the patient. Additionally, when the monitoring is done at a central facility a single nurse can monitor multiple patients which can result in decreased staffing requirements.

Generally speaking, electronic monitors work by first sensing an initial status of a patient, and then generating a signal when that status changes, e.g., he or she has sat up in bed, left the bed, risen from a chair, etc., any of which situations could pose a potential cause for concern in the case of an at-risk patient. Electronic bed and chair monitors typically use a pressure sensitive switch in combination with a separate monitor/microprocessor. In a common arrangement, a patient's weight resting on a pressure sensitive mat (i.e., a "sensing" mat) completes an electrical circuit, thereby signaling the presence of the patient to the microprocessor. When the weight is removed from the pressure sensitive switch, the electrical circuit is interrupted, which fact is sensed by the microprocessor. The software logic that drives the monitor is typically programmed to respond to the now-opened circuit by triggering some sort of alarm—either electronically (e.g., to the nursing station via a conventional nurse call system) or audibly (via a built-in siren).

General information relating to mats for use in patient monitoring may be found in patent application Ser. No. 09/285,956 filed Apr. 2, 1999, now U.S. Pat. No. 6,307,476, the disclosure of which is specifically incorporated herein by reference. Additionally, U.S. Pat. Nos. 4,179,692, 4,295,133, 4,700,180, 5,600,108, 5,633,627, 5,640,145, and 5,654,694 (concerning electronic monitors generally) contain further information generally pertinent to this same subject matter, as do U.S. Pat. Nos. 4,484,043, 4,565,910, 5,554,835, and 5,623,760 (switch patents), the disclosures of all of which are all incorporated herein by reference.

By way of general background, in a typical arrangement, a pressure-sensing mat is a sealed "sandwich" composed of three layers: two outer layers and an inner (central) layer positioned therebetween. The outer layers are usually made of some sort of plastic and are impermeable to fluids and electrically non-conductive on their outer faces, where "outer" is determined with respect to the middle layer. The inner surface of each of the outer layers—which inner surfaces are oriented to face each other from opposite sides of the central layer—is made to be electrically conductive, usually by printing a conductive (e.g., carbon-based) ink on that surface. The compressible middle "central spacer" is made of a non-conductive material and serves to keep the two conductive faces apart when a patient is not present on the sensor. The central spacer is discontinuous, which makes it possible for the two conductive inner surfaces to be forced into contact through the discontinuities when weight is applied to the switch. By attaching a separate electrical lead to each of the conductive inner faces, it can readily be determined (e.g., via a simple continuity check) whether a weight is present on the sensor (e.g., whether a patient is seated thereon). Removal of the weight causes the central spacer to expand and press apart the two conducting faces, thereby breaking the electrical connection between them. Thus, a device that monitors the resistance across the two electrical leads may determine when a patient has risen to his or her feet.

One disadvantage of the current generation of pressure sensitive mats is that they cannot be completely (e.g., hermetically) sealed against the external environment. The reason for this should be clear: if the interior of the mat were completely sealed, air pressure inside of the mat would tend to oppose the urging of the mat faces into contact, thereby making it difficult or impossible to complete the circuit (e.g., think of compressing an "air pillow"). Thus, it is customary to intentionally leave gaps in the seal between the two halves of the mat which allow for movement of air into and out of the switch.

Another disadvantage of the prior art is that partial sealing of the perimeter of the mat can cause it to resist expansion after weight is removed therefrom. That is, when a patient places weight on a conventional mat, air is slowly expelled from the mat interior, typically through a small opening in the perimeter of the mat. However, when the patient rises the opening in the mat can collapse or narrow in response to air pressure on the now-deflated mat body, thereby retarding the process of reinflating it. As a consequence, the mat may continue to signal that the patient is still present on the mat for a time after he or she has risen.

Of course, the fact that the interior of the mat must kept open to the atmosphere results in a mat that is highly susceptible to invasion by bodily fluids or cleaning solutions, as the in-rushing air tends to carry fluids along with it into the interior of the mat. Further, it is well known that some common disinfecting cleaners can loosen the adhesives that hold the layers of the mat together, thereby ruining the sensor. Thus, cleaning soiled mats that have air passages placed therein becomes problematic. In summary, what is needed is a pressure sensitive mat that is more resistant to invasion by fluids than is presently available.

Heretofore, as is well known in the patient monitoring arts, there has been a need for an invention to address and solve the above-described problems. Accordingly, it should now be recognized, as was recognized by the present inventors, that there exists, and has existed for some time, a very real need for pressure sensitive mat and monitoring system that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

In accordance with a first aspect of the instant invention, there is provided a pressure sensitive mat which has preferably been completely sealed around its exterior edges except where a breathing tube passes therethrough. The interior of the mat is kept in communication with the atmosphere by way, of a section of flexible tubing which encloses the attached electrical line. One end of the tubing is sealed inside of the mat and the other end is open to the atmosphere, thereby providing a passageway for air to reach the interior of the mat. This arrangement, however, protects the interior of the mat from exposure to fluids that might be present near its perimeter. In fact, this innovation allows the mat-portion of the invention to be completely submersed without adverse effect, if that should be come necessary.

According to another aspect of the instant invention, there is provided a pressure sensitive mat and breathing tube combination wherein the wires that transmit status information from the interior of the mat to a separate electronic monitor are not inside of the breathing tube, but instead are adjacent to it through at least part of their length. One example of such an arrangement would be found in a multi-lumen tube of the sort that are well known to those skilled in the medical arts, wherein the electrical wires are preferably placed in one tube (or lumen), with one or more other tubes being kept clear to permit the passage of air therethrough.

Finally, according to still another aspect of the instant invention, there is provided a pressure sensitive mat and breathing tube combination, wherein the breathing tube is completely separated from the electrical wires and separately penetrates the mat perimeter to reach its interior.

The foregoing has outlined in broad terms the more important features of the invention disclosed herein so that the detailed description that follows may be more clearly understood, and so that the contribution of the instant inventor to the art may be better appreciated. Although the instant invention will be described in connection with a preferred embodiment, it is to be understood that it is not intended to limit the invention to that embodiment. That is, the instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Further, it should be understood that the phraseology and terminology employed herein are for the purpose of description and should not be regarded as limiting, unless the specification specifically so limits the invention. Finally, the disclosure that follows is intended to apply to all alternatives, modifications and equivalents as may be included within the spirit and scope of the invention as defined by the appended claims.

BRIEF DESCRIPTION OF THE DRAWINGS

Other objects and advantages of the invention will become apparent upon reading the following detailed description and upon reference to the drawings in which.

DETAILED DESCRIPTION OF THE INVENTION

General Background

Figure 1:
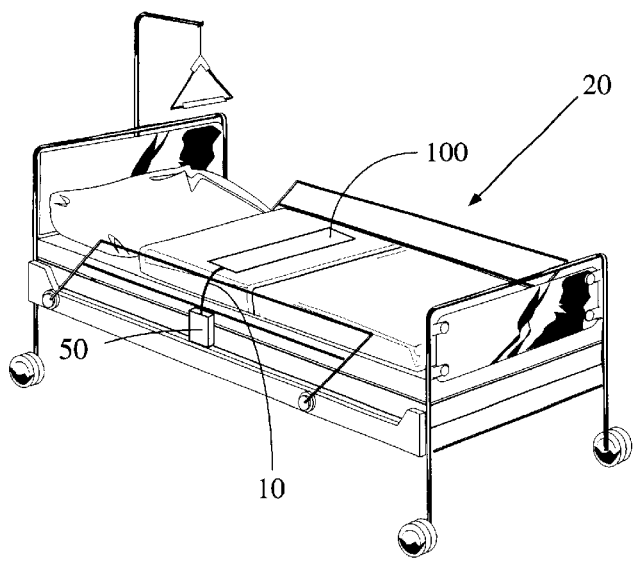
FIG. 1 illustrates the general environment of the invention.

Turning first to FIG. 1 wherein the general environment of the instant invention is illustrated, in a typical arrangement a sensing mat 100 is placed on a hospital bed 20 where it will lie beneath a weight-bearing portion of the reclining patient's body, usually the buttocks and/or shoulders. It should be noted at the outset, however, that although the language that follows is largely confined to illustrations involving bed-type sensors, the range of application of the instant invention is much broader and could include chair sensors, potty sensors, and any other type of pressure-sensitive switch that is used in a patient monitoring environment where invasion by fluids is a concern.

Figure 2:
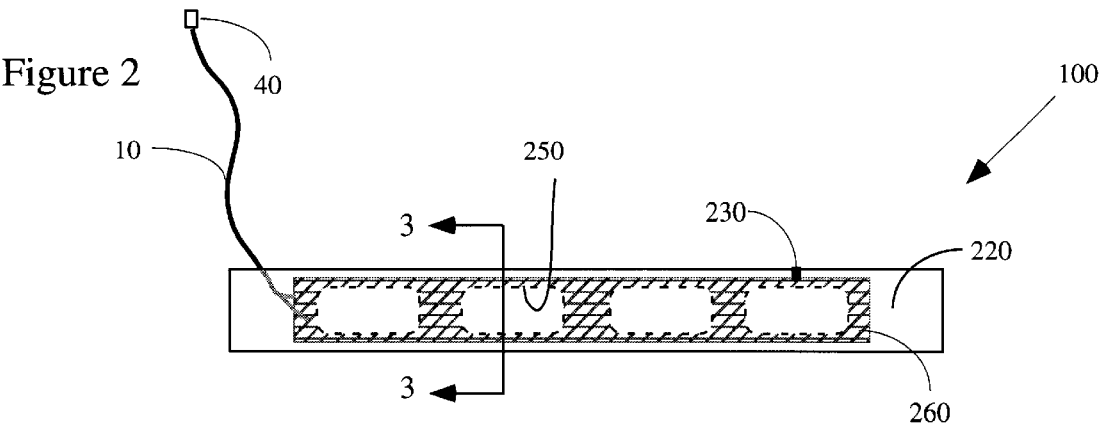
FIG. 2 contains a schematic illustration of a convention pressure sensitive mat.

Generally speaking, the mat 100/monitor 50 combination works as follows. When a patient is placed atop the mat 100, the patient's weight compresses the mat 100 and closes an electrical circuit, which closure is sensed by the attached electronic patient monitor 50 through electrical line 10 and connector 40 (FIG. 2). When the patient attempts to leave the bed, weight is removed from the sensing mat 100, thereby breaking the electrical circuit. The patient monitor 50 senses the change in electrical continuity and signals the caregiver per its pre-programmed instructions. Note that additional electronic connections not pictured in this figure might include a monitor 50 to nurse-call-station connection, a monitor 50 to computer connection, and an A/C power cord—although the monitor 50 can certainly be configured to be battery operated.

FIG. 2 contains a schematic drawing of a prior art pressure sensitive patient mat. As is indicated in that figure, a typical pressure sensitive mat 100 includes upper and lower non-conductive outer members 220 and 240 (FIG. 3), respectively, which serve to protect the interior from contact with the environment. These members are usually made of a flexible impermeable electrically non-conductive material such as plastic, with polyester being the preferred material. These two members are separated by an internal non-conductive spacer 260, which has at least one aperture therethrough 250. In FIG. 2, the central spacer 260 is shown in phantom because it is hidden from view within the assembled product.

Figure 3:
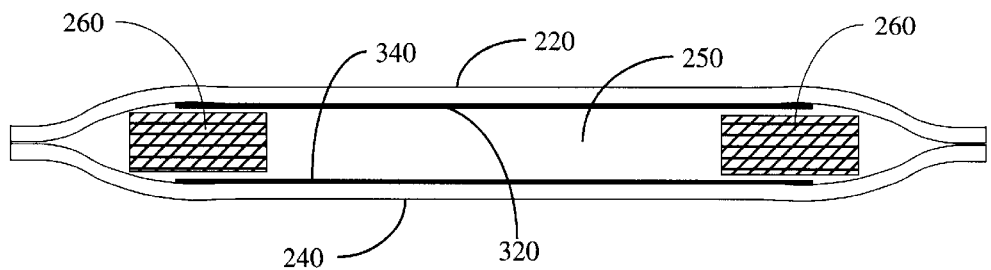
FIG. 3 contains a cross-sectional view of a pressure sensitive mat.

As is further indicated in FIG. 3, the typical pressure sensitive switch is a "sandwich" type arrangement with the two outer members surrounding the inner non-conductive spacer 260. The perimeters of the upper 220 and lower 240 members are conventionally sealed together by a heat activated adhesive (such as polyethylene) or by some form of pressure sensitive adhesive.

Affixed to the inner surface of each of the outer members 220 and 240 is a conductive layer (320 and 340, respectively) which, for safety purposes, preferably does not extend to the edges of the mat. As should be clear, pressure on the mat 100 tends to urge the conductive faces 320 and 340 into contact through aperture 250, thereby completing an electrical circuit. When pressure is released, the central spacer 260, which is preferably constructed of a compressible and resilient material, expands and pushes the conductive layers apart. As is suggested in FIG. 2, when the electrical line 10 enters the mat it is typically separated into two electrically isolated elements, one of which is placed in electrical communication with the conductive layer 320 atop of the spacer 260 and the other which is placed in electrical communication with the conductive layer 340 underneath the spacer.

As is generally illustrated in FIG. 3, the central spacer 260 usually fits loosely within an envelope formed by the two outer layers 220 and 240. This arrangement allows air to move freely throughout the interior of the mat 100. Fluid communication between the interior of the mat and the atmosphere is typically provided in the form of one or more breaches in the seal between the upper 220 and lower 240 members. These breaches are created during the manufacturing process and provide a means for the mat 100 to "breathe" when compressed. A first natural breach occurs at the point where electrical line 10 enters the mat between the upper 220 and lower 240 mat members. Typically, the mat material fits loosely around the electrical line 10, thereby providing a ready passageway for air (and fluids) to enter and exit the mat. Where more airways are needed, it is possible to create gaps between the outer members along their common perimeter. One way of doing this involves placing a piece of monofilament line between the upper 220 and 240 members before they are sealed. After the two members have been sealed together, the line is withdrawn, leaving behind a small gap 230 in the seal between the layers.

Preferred Mat Embodiments

Figure 4:
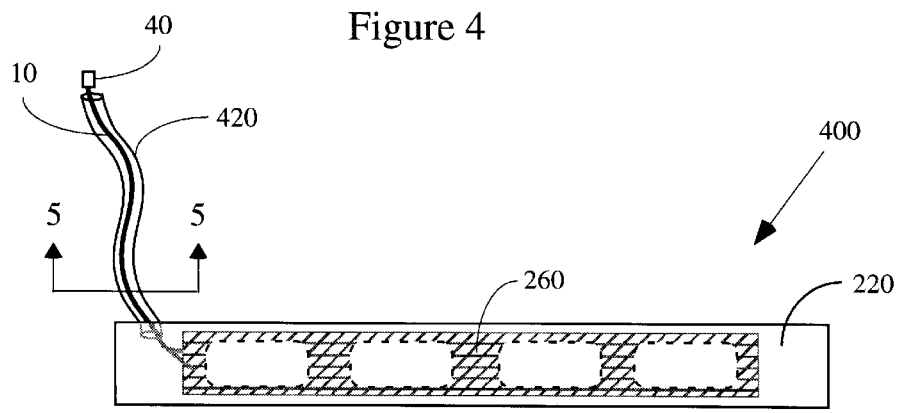
FIG. 4 illustrates a preferred embodiment of the instant invention.

A first preferred embodiment of the instant mat is illustrated in FIG. 4, which contains a plan view of the device. As is illustrated there, the mat portion of the sensor 400 is configured in a "sandwich" arrangement as has been described above. However, the instant embodiment differs from the prior art in that it contains a separate open-ended "breathing tube" 420 which loosely encloses the electrical line 10. This tube 420 enters the mat between the upper 220 and lower 240 members. The upper 220 and lower 240 members may now be completely sealed along their perimeters, including where the tube 420/electrical line 10 combination enters the mat 400. When pressure is applied to the mat 400, the air inside of the mat 400 is pushed toward and out of the breathing tube 420, thereby allowing the mat 400 to compress. Similarly, when pressure is removed, air returns from the atmosphere to the interior of the mat 400 via the same conduit, thereby allowing the mat 400 to quickly expand to its un-weighted configuration which separates the upper 220 and lower 240 members.

Figure 5:
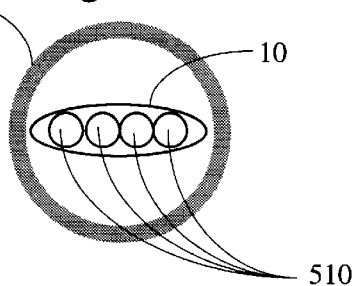
FIG. 5 contains a cross-sectional view of a preferred connecting tube arrangement of the instant invention, wherein the tube encloses the electrical wire.

FIG. 5 illustrates a preferred embodiment of the breathing tube 420 in cross section. As can be seen in this figure, tube 420 is sized so that the electrical line 10 fits loosely therein, thereby providing at least a partially unobstructed air passageway. The breathing tube 420 is preferably round or oval, although obviously the precise shape of the tube 420 is unimportant, so long as an air-tight seal may be created around the perimeter of the tube 420 where it enters the mat 400 between the two outer mat members. Within electrical line 10 will typically be found two or more electrically isolated conductors 510, with the use of a four-conductor wire being a common arrangement. It should be apparent that the number of electrical conductors 510 that might be found within the electrical line 10 is unimportant to the practice of the instant invention. As has been described previously, it is customary to use two of these conductors 510 to establish separate electrical communications between the monitor 50 and the upper 320 and lower 340 conducting members inside of the mat.

In operation, the sensing portion of the instant invention 400 may be completely submerged without risk of fluid invasion, so long as the outer terminus of the breathing tube 420 (i.e., the end nearest the connector 40) is kept clear of the fluid. Further, the instant mat 400 may be fully compressed and then released while held under water without risk of drawing fluid into its interior, provided that the perimeter has been completely sealed. Finally, in a patient monitoring situation where there has been a release of fluid into the bed or chair, the mat 400 can be cleaned and reused without endangering its structural integrity.

Figure 6A:
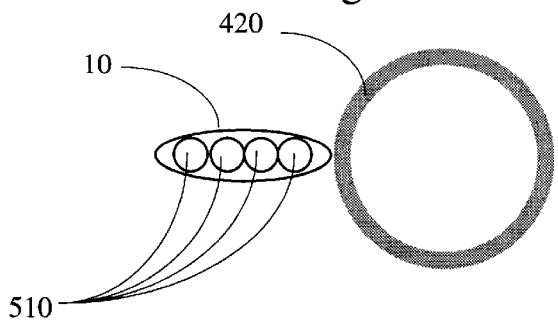
FIGS. 6A and 6B illustrate cross sections of another wire/tube configuration, wherein the electrical wire and tube are run roughly in parallel.
Figure 6B:
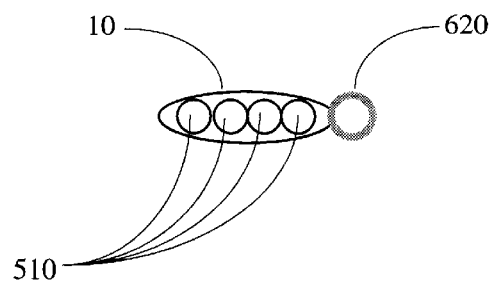
Figure 7:
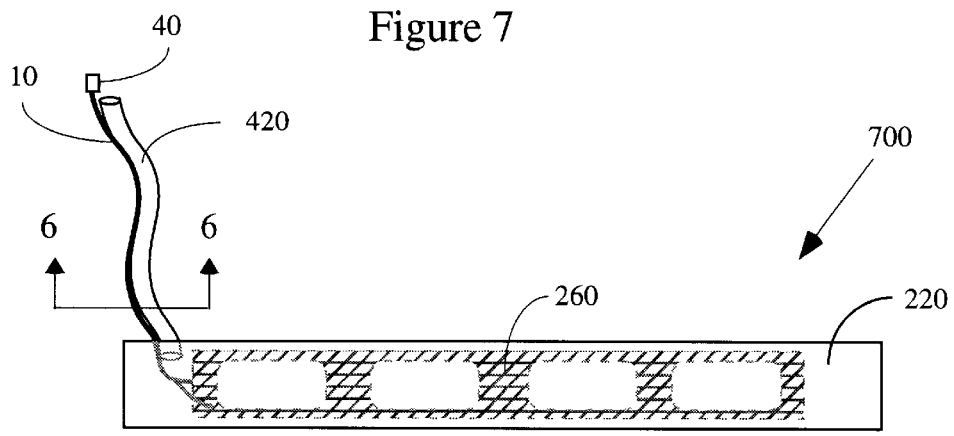
FIG. 7 contains a plan view of another preferred embodiment, wherein the electrical wire and breathing tube are run roughly in parallel.

FIG. 7 contains another preferred arrangement. In this variation, the tube 420 and electrical wire 10 run roughly in parallel into the mat 700. A cross sectional view of this arrangement may be found in FIGS. 6A and 6B, these two figures differing only in the size of the breathing tubes 420 and 620 attached thereto. This configuration of breathing tube/electrical conductors 510 is sometimes referred to as a "multi-lumen" cable by those skilled in the art. Of course, the diameter of the breathing tube 420 is unimportant to the operation of the instant invention, except that it should be large enough to convey sufficient air into and out of the interior of the mat 700 to allow it to be readily compressed and then expanded again. The best tube 420 diameter will ultimately depend on the specifics of the mat to which it is attached and will need to be determined empirically for each type of mat.

Figure 8:
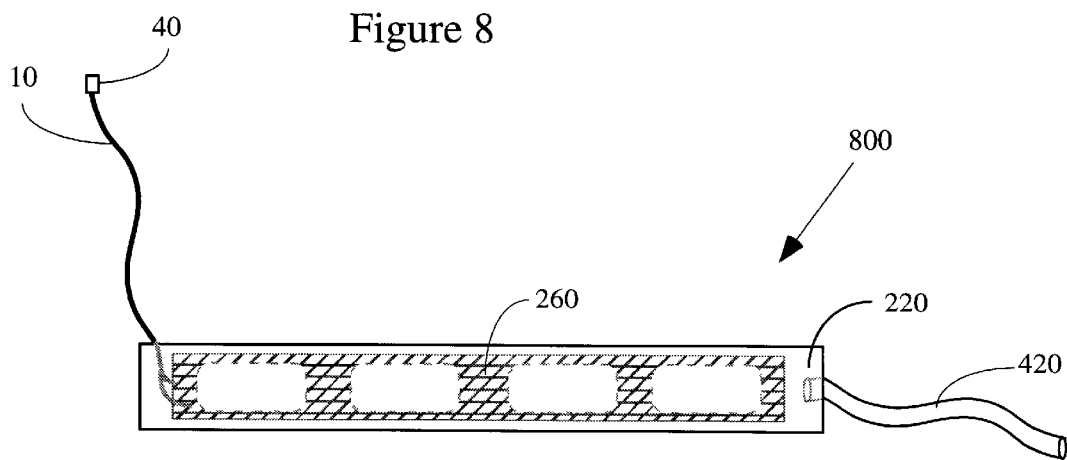
FIG. 8 illustrates another preferred arrangement, wherein the electrical wire and breathing tube enter the mat in different locations.

FIG. 8 contains still another variation, wherein the electrical line 10 and the breathing tube 420 enter the mat 800 independently. As should be clear from this figure, this arrangement suffers from the disadvantage that two different breaches of the mat perimeter would need to be sealed. However, having the electrical line 10 and breathing tube 420 separated might be advantageous in some circumstances.

Finally, it should be noted and remembered that although it is preferable that the mat be completely sealed along its perimeter except where the breathing tube penetrates it, that is not strictly required. The breathing tube acts to assist in reinflation of the any sort of mat when weight is removed therefrom, so it would also be useful with a conventional mat which is not hermetically sealed. However, if the mat is not completely sealed along its perimeter there is a risk that fluid will enter the interior of the mat through those breaches, as has been a problem in the past.

Clearly, many variations of this and the previous arrangements are possible and have been specifically contemplated by the instant inventor.

CONCLUSIONS

Although the preceding text has occasionally referred to the sensor of the instant invention as a "bed" mat that was done for purposes of specificity only and not out of any intention to limit the instant invention to that one application. In fact, the potential range of uses of this invention is much broader than bed-monitoring alone and might include, for example, use with a chair monitor, urinal monitor, or other pressure sensitive patient monitor application which is configurable as a binary switch, a binary switch being one that is capable of sensing at least two conditions and responding to same via distinct electronic signals. In the preferred embodiment, those two conditions would be the presence of weight on the switch. Additionally, it should be noted that the use of the term "binary" is not intended to limit the instant invention to use only with sensors that can send only two signal types. Instead, binary switch will be used herein in its broadest sense to refer to any sort of sensor that can be utilized to sense the condition or location of a patient, even if that sensor can generate a multitude of different signals.

Thus, it is apparent that there has been provided, in accordance with the invention, a patient sensor and method of operation of the sensor that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. A device for use with an electronic patient monitor and for detecting a presence or an absence of a patient, comprising:

(a) a pressure sensitive binary switch,
    said binary switch having an upper member and a lower member being joined together along a common perimeter,
    said upper and said lower members together defining an interior of said binary switch and said binary switch being responsive to at least two conditions;
(b) an electrical line in electrical communication with said interior of said binary switch,
    said electrical line being for the transmission of said response of said binary switch to said electronic patient monitor, and,
    said electrical line penetrating said perimeter of said binary switch between said upper and lower members; and,
(c) a breathing tube,
    said breathing tube having a first terminus and a second terminus,
    said first terminus being in fluid communication with said interior of said binary switch and said second terminus being in fluid communication with the atmosphere,
    wherein said breathing tube enters said binary switch between said upper member and said lower member, and,
    wherein said perimeter of said binary switch is substantially sealed except where said breathing tube and said electrical line enter said interior of said binary switch.

2. An apparatus according to claim 1, wherein said pressure sensitive binary switch is suitable for use on a device selected from the group consisting of a bed, a chair, and a toilet.

3. An apparatus according to claim 1, wherein said electrical line contains at least two electrically isolated conductors.

4. An apparatus according to claim 3, wherein said upper member has a inner conductive surface, and said lower member has an inner conductive surface,
    wherein said upper and lower member inner conductive surfaces are positionable to be proximate to each other, and,
    wherein said upper and lower member inner conductive surfaces are positionable to face each other across said interior of said binary switch, and,
wherein said electrical line has a first conductor and a second conductor,
    said first conductor being in electrical communication with said upper member inner conductive surface and said second conductor being in electrical communications with said lower member inner conductive surface.

5. An apparatus according to claim 1, wherein said breathing tube is proximate to said electrical line where said breathing tube penetrates said perimeter of said binary switch.

6. An apparatus according to claim 5, wherein said breathing tube encloses said electrical line.

7. An apparatus according to claim 1, wherein said upper member and said lower member are substantially planar.

8. An apparatus according to claim 1, wherein said electrical line and said breathing tube taken together are a multi-lumen cable.

9. A device for detecting a presence or an absence of a patient, comprising:

(a) a pressure sensitive binary switch,
    said binary switch having an upper member and a lower member, said binary switch having an interior and a perimeter, said perimeter being defined where said upper member and said lower member are joined together, and said binary switch being responsive to at least two conditions,
  (a1) a first condition corresponding to said presence of the patient on said binary switch, and,
  (a2) a second condition corresponding to said absence of the patient from said binary switch;
(b) an electrical line in electrical communication with said interior of said binary switch,
  said electrical line passing into said interior of said binary switch along said perimeter and between said upper member and said lower member,
  said electrical line having an enclosed terminus and a remote terminus,
  said enclosed terminus being within said interior of said binary switch and said remote terminus being outside said binary switch;
(c) a breathing tube, said breathing tube providing a passageway for air into and out of said interior of said binary switch, said perimeter of said binary switch being completely sealed except where said breathing tube and said electrical line penetrates it; and,
(d) an electronic patient monitor, said electronic patient monitor being in electrical communication with said remote terminus of said electrical line, said electrical monitor for at least sensing said first and said second condition of said binary switch and being responsive thereto.

10. An apparatus according to claim 9, wherein said pressure sensitive binary switch is suitable for use on a device selected from the group consisting of a bed, a chair, and a toilet.

11. An apparatus according to claim 9, wherein said electrical line contains at least two electrically isolated conductors.

12. An apparatus according to claim 11, wherein said upper member has a inner conductive surface, and said lower member has an inner conductive surface,
  wherein said upper and lower member inner conductive surfaces are positionable to be proximate to each other within said interior of said binary switch, and,
  wherein said upper and lower member inner conductive surfaces are positionable to face each other across said interior of said binary switch, and,
  wherein said electrical line has a first conductor and a second conductor,
    said first conductor being in electrical communication with said upper member inner conductive surface and said second conductor being in electrical communications with said lower member inner conductive surface.

13. An apparatus according to claim 9, wherein said breathing tube is proximate to said electrical line where said electrical line penetrates said perimeter of said binary switch.

14. An apparatus according to claim 13, wherein said breathing tube encloses said electrical line.

15. A device for detecting a presence or an absence of a patient, comprising:

(a) a pressure sensitive binary switch having an interior and a perimeter, said binary switch having an substantially planar upper member and a substantially planar lower member, wherein
  said upper member and said lower member together define at least a portion of said interior of said binary switch,
  at least a portion of a periphery of said upper member and a periphery of said lower member are joined together, and
  at least a portion of said perimeter is formed where said upper member periphery and said lower member periphery are joined together;
(b) an electrical line in electrical communication with said interior of said binary switch,
  said electrical line passing into said interior of said binary switch along said perimeter between said upper member and said lower member; and,
(c) a breathing tube for providing a passageway for air into and out of said interior of said binary switch, said breathing tube having a first terminus and a second terminus,
  said first terminus being in fluid communication with said interior of said binary switch,
  said second terminus being in fluid communication with the atmosphere and extending outwardly beyond said perimeter of said binary switch, said perimeter of said binary switch being completely sealed except where said breathing tube and said electrical line penetrates it.

16. An apparatus according to claim 15, wherein said pressure sensitive binary switch is suitable for use on a device selected from the group consisting of a bed, a chair, and a toilet.

17. An apparatus according to claim 15, wherein said electrical line contains at least two electrically isolated conductors.

18. An apparatus according to claim 15, wherein said upper member has a inner conductive surface, and said lower member has an inner conductive surface,
  wherein said upper and lower member inner conductive surfaces are positionable to be proximate to each other, and,
  wherein said upper and lower member inner conductive surfaces are positionable to face each other across said interior of said binary switch, and,
  wherein said electrical line has a first conductor and a second conductor,
    said first conductor being in electrical communication with said upper member inner conductive surface and said second conductor being in electrical communications with said lower member inner conductive surface.

19. An apparatus according to claim 15, wherein said breathing tube is proximate to said electrical line where said breathing tube penetrates said perimeter of said binary switch.

20. An apparatus according to claim 19, wherein said breathing tube encloses said electrical line.

* * * * *